United States Patent [19]

Grandjean

[11] Patent Number: 5,089,019
[45] Date of Patent: Feb. 18, 1992

[54] MUSCLE WORK OUTPUT MONITOR BY INTRAMUSCULAR TEMPERATURE VARIATION MEASUREMENT

[75] Inventor: Pierre A. Grandjean, Bassenge, Belgium

[73] Assignee: Medtronic, Inc., Minneapolis, Minn.

[21] Appl. No.: 446,592

[22] Filed: Dec. 6, 1989

[51] Int. Cl.⁵ .............................................. A61M 1/10
[52] U.S. Cl. ......................................... 623/3; 600/16
[58] Field of Search .................. 623/3; 600/16, 17, 18

[56] References Cited

U.S. PATENT DOCUMENTS

| | | | |
|---|---|---|---|
| 4,143,661 | 3/1979 | LaForge et al. | 128/419 R |
| 4,384,829 | 5/1983 | Conley et al. | 623/3 |
| 4,453,537 | 6/1984 | Spitzer | 600/17 |
| 4,457,673 | 7/1984 | Conley et al. | 623/3 |
| 4,666,443 | 5/1987 | Portner | 500/16 |
| 4,685,446 | 8/1987 | Choy | 600/18 |
| 4,771,765 | 9/1988 | Choy et al. | 600/18 |
| 4,936,304 | 6/1990 | Kresh et al. | 128/419 PG |

Primary Examiner—Randy C. Shay
Attorney, Agent, or Firm—John L. Rooney

[57] ABSTRACT

Apparatus and method for monitoring performance of a skeletal muscle powered cardiac assist system. A chronically implantable temperature sensor is imbedded within the skeletal muscle. Muscle contraction and performance can be monitored by intramuscular temperature measurement. The temperature measurements are used by the implantable pulse generator of the cardiac assist system to maximize efficiency in the use of the skeletal muscle by optimizing timing of conditioning, maintenance, and stimulation pulses.

6 Claims, 9 Drawing Sheets

MUSCLE WORK OUTPUT MONITOR BY INTRAMUSCULAR TEMPERATURE VARIATION MEASUREMENT

CROSS REFERENCES TO CO-PENDING APPLICATIONS

This application is related to Serial No. 07/446,594 Filed Dec. 6, 1989, currently pending, entitled "Steroid Eluting Intramuscular Lead" by the same assignee; Ser. No. 07/446,811, Filed Dec. 6, 1989, currently pending, entitled "Muscle Contraction Control by Intramuscular Pressure Monitoring" by the same assignee; and Ser. No. 07/446,593, filed Dec. 6, 1989, now currently pending, entitled "Muscle Fitness Detection by Colorimetry" by the same assignee.

BACKGROUND OF THE INVENTION

1. Field of the Invention

The present invention relates generally to cardiac assist systems, and more particularly, relates to monitoring of cardiac assist systems which are powered by skeletal muscle.

2. Description of the Prior Art

Cardiac assist systems do not replace the human heart, but merely supplement it. Many techniques have been proposed using a variety of mechanical power sources. Typically these require some form of percutaneous energy transfer because of the difficulty in storing sufficient energy subcutaneously. Such systems are cumbersome and inconvenient for the patient, and are prone to infection along the percutaneous energy transfer path.

A technique holding a great deal of promise is to power the cardiac assist system from a surgically modified skeletal muscle. The cardiac assist system is thus powered by normal biochemical processes. U.S. Pat. No. 4,813,952 issued to Khalafalla teaches a number of configurations of a skeletal muscle powered cardiac assist system.

One problem peculiar to a skeletal muscle powered cardiac assist system is that the skeletal muscle must be conditioned to the constant load of continuous contraction/relaxation demanded of the myocardium U.S. Pat. No 4,411,268 issued to Cox teaches a technique for conditioning the skeletal muscle. Whereas the apparatus of Cox is effective to accomplish this conditioning, his system has no provisions for chronically monitoring the stability of the skeletal muscle following the conditioning process In practice this necessitates the attention of highly skilled medical personnel to monitor the operation of the skeletal muscle with sophisticated instrumentation, and to exercise manual control of the stimulation regimen with pulse generator programming equipment. Furthermore, neither Cox nor Khalafalla teach a real time monitoring mechanism, whereby the timing of the conditioning, maintenance, and stimulation pulses may be automatically adjusted to optimize efficiency of skeletal muscle contractions.

SUMMARY OF THE INVENTION

The preferred mode of the present invention employs a chronically implantable temperature sensor which is positioned within the skeletal muscle of a cardiac assist system. The sensor preferably employs a thermoresistive device, such as a thermistor, coupled to the implantable pulse generator of the cardiac assist system.

A circuit in the implantable pulse generator senses the changes in resistance of the thermistor which correspond to temperature changes within the skeletal muscle. The implantable pulse generator is thus able to monitor the efficiency of the work output of the skeletal muscle.

Circuitry within the implantable pulse generator changes the timing and characteristics of the generated pulses in relation to naturally occurring and paced heart contractions to optimize muscle activity. This improves the efficiency of the cardiac assist system by minimizing parasitic heat production. It also ensures that the myocardium obtains maximum assistance from contractions of the skeletal muscle.

BRIEF DESCRIPTION OF THE DRAWINGS

Other objects of the present invention and many of the attendant advantages of the present invention will be readily appreciated as the same become better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

The present invention employs a temperature sensor implanted within the skeletal muscle of a skeletal muscle-powered cardiac assist system to chronically monitor the adequacy of skeletal muscle conditioning/maintenance and the. proper timing of skeletal muscle stimulation pulses. The cardiac assist system may be configured in a variety of ways as described in U.S. Pat. No. 4,813,952 issued to Khalafalla, herein incorporated by reference. Several of these configurations are discussed herein by way of illustration and are not intended to limit the present invention.

Figure 1:
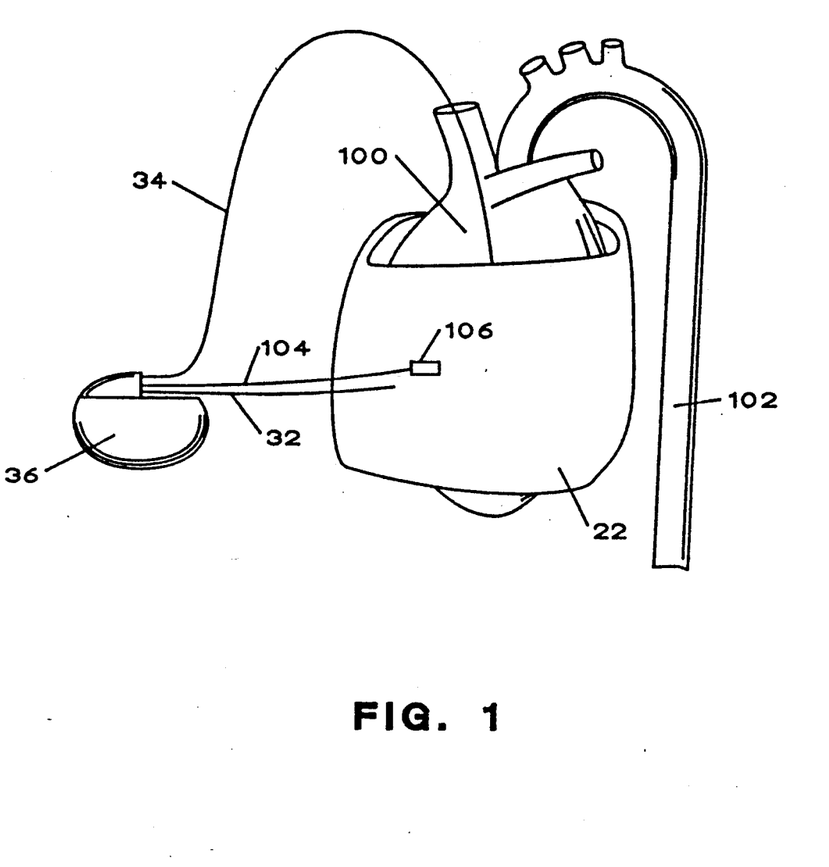
FIG. 1 is a first embodiment of the present invention wherein the skeletal muscle is wrapped about the myocardium.

FIG. 1 is an embodiment of the present invention wherein skeletal muscle 22 is wrapped about human heart 100. Skeletal muscle 22 is conditioned as a "slow twitch" muscle as described by Cox in U.S. Pat. No.

4,411,268, herein incorporated by reference. Adequacy of conditioning and maintenance of this state is monitored in the manner described below. Implantable pulse generator 36 is coupled to pacing lead 34 to produce a demand pacemaker as taught by Cox. In addition, implantable pulse generator 36 stimulates skeletal muscle 22 to contract in synchrony with human heart 100. Assistance to human heart 100 is provided by the simultaneous contraction of skeletal muscle 2 to increase systolic pressure in descending aorta 102 and elsewhere in the circulatory system.

According to the present invention, a temperature sensor 106 is implanted within skeletal muscle 22 to monitor operation of the cardiac assist system. The temperature as measured by temperature sensor 106 is transferred to implantable pulse generator 36 via lead 104. This data is used by implantable pulse generator 36 to properly time stimulation, conditioning, and maintenance pulses.

Figure 2:
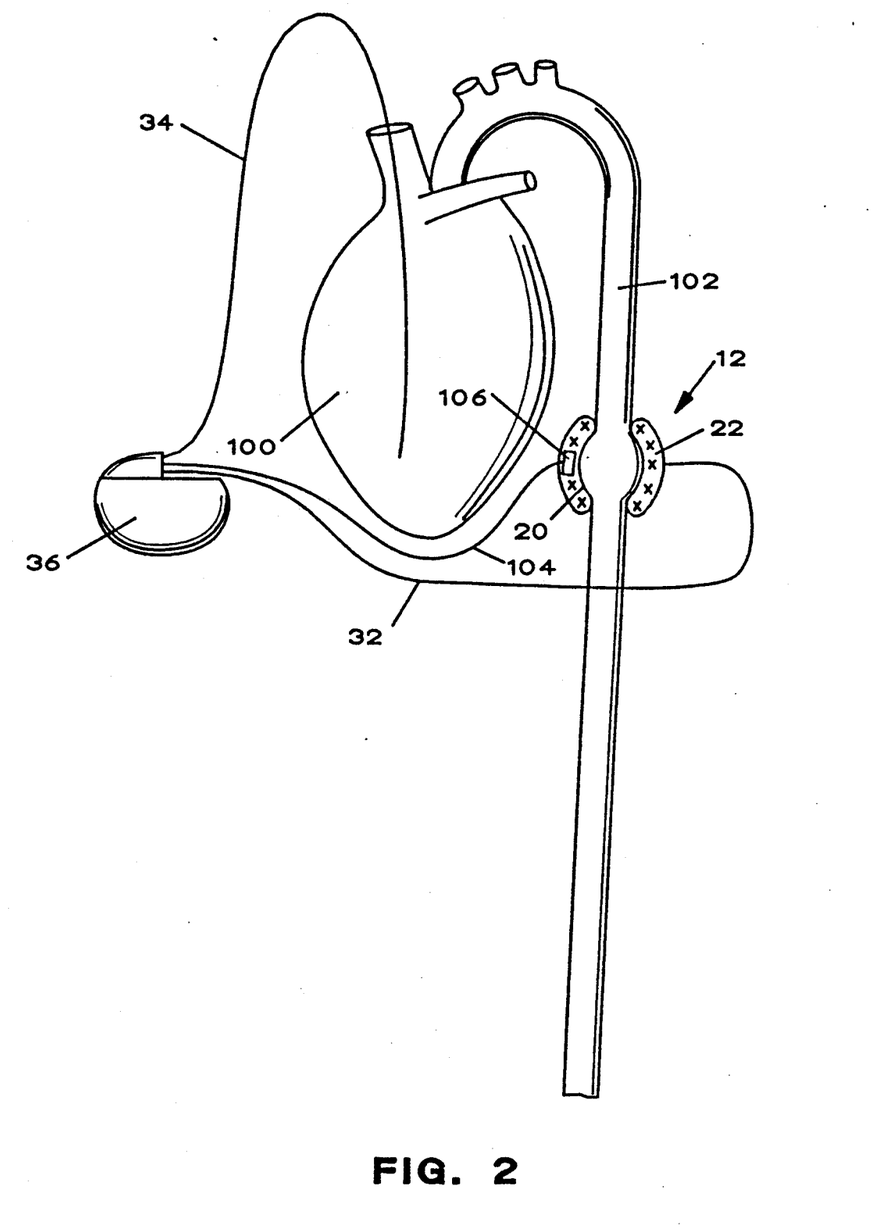
FIG. 2 is an alternative embodiment of the present invention wherein the skeletal muscle is wrapped about the descending aorta.

FIG. 2 is an alternative embodiment of the present invention. In this embodiment skeletal muscle 22 is wrapped about artificial chamber 20 inserted in series with descending aorta 102. Unlike the embodiment of FIG. 1, implantable pulse generator 36 stimulates skeletal muscle 22 to contract following evacuation of human heart 100. This is accomplished by the insertion of a delay between a paced or sensed beat of human heart 100 and the stimulation of skeletal muscle 22 as discussed below.

Figure 3:
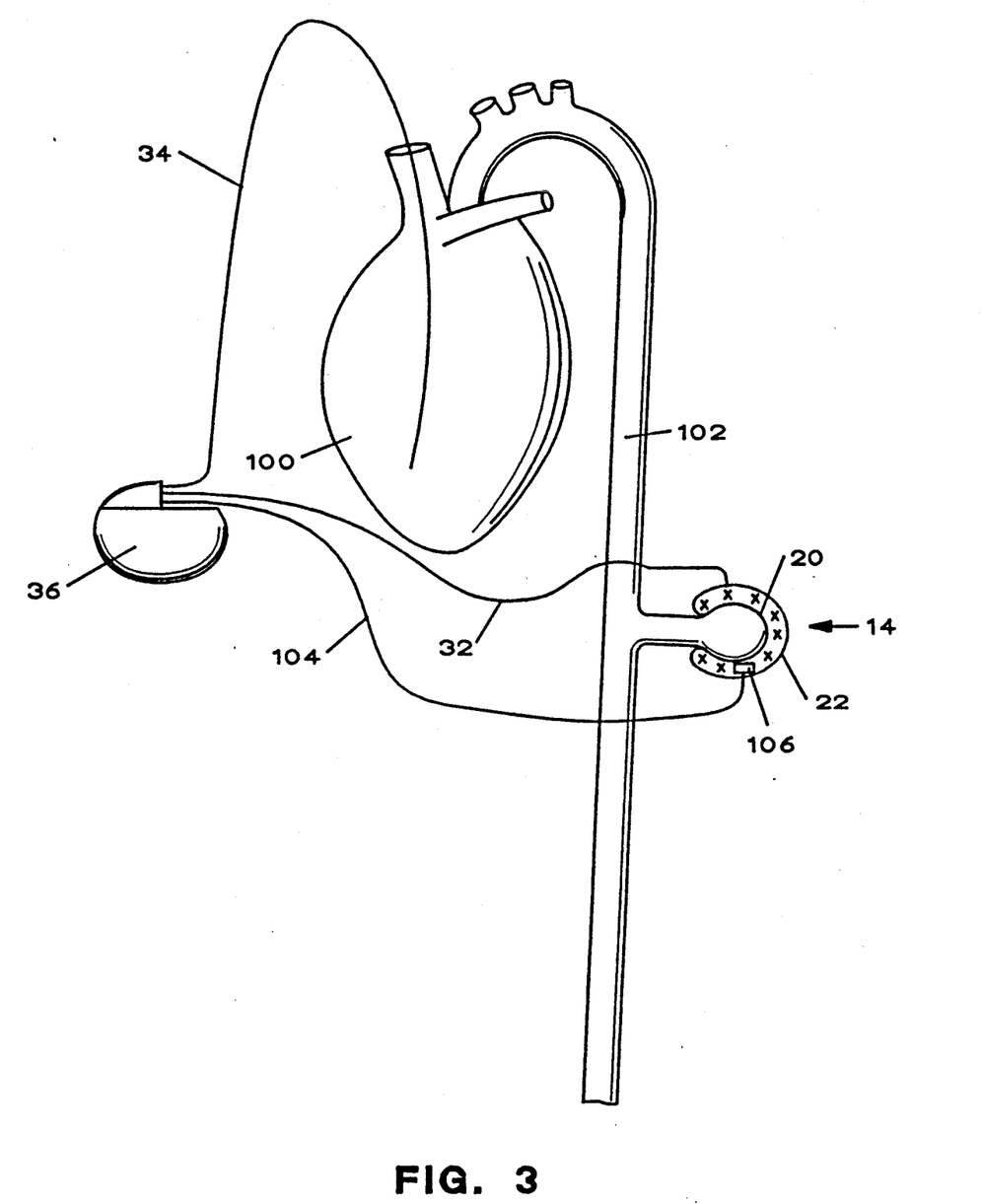
FIG. 3 is an alternative embodiment of the present invention Wherein the skeletal muscle performs counter pulsation of the descending aorta.

FIG. 3 is a further embodiment wherein artificial chamber 20 is coupled external to descending aorta 102. In this configuration skeletal muscle 22 is stimulated to counter pulse human heart 100. This raises diastolic pressure, thereby increasing perfusion of human heart 100. This is accomplished by the generation by implantable pulse generator 36 of a sufficient delay between a sensed or paced contraction of human heart 100 and stimulation of skeletal muscle 22 to cause the desired counter pulsation.

Figure 4:
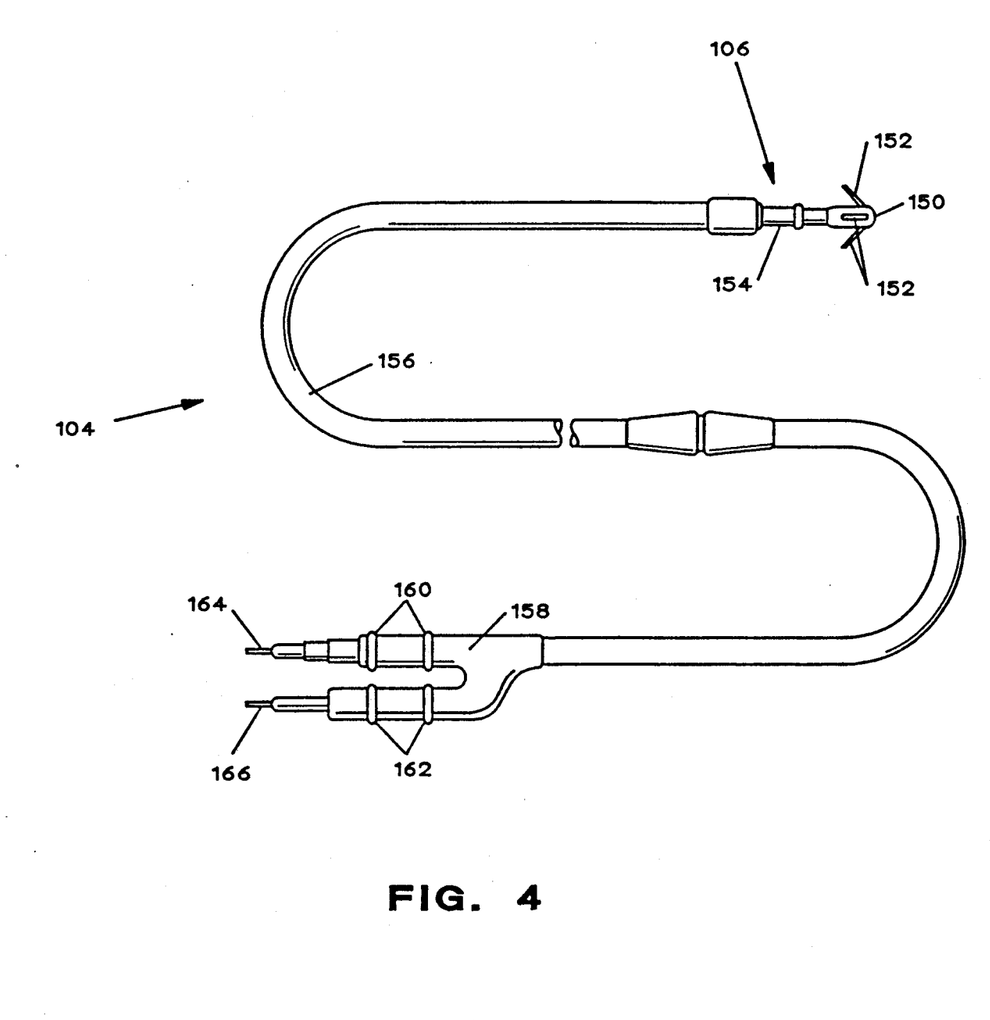
FIG. 4 is a plan view of the sensing lead with temperature sensor attached.

FIG. 4 is a plan view of lead 104 with temperature sensor 106 attached to the distal end. The outer covering of lead 1 104 is outer sheath 156 which is of a chronically implantable biocompatible material such as medical grade silicone rubber or polyurethane. The proximal end of lead 104 contains bifurcated connector 158 which sealingly inserts into implantable pulse generator 36. Sealing ring pairs 160 and 162 complete the seal against the ingress of bodily fluids. Lead 104 contains two electrically separated conductors which couple the thermistor of temperature sensor 106 with implantable pulse generator 36. These two conductors are electrically coupled to terminal pins 164 and 166.

The distal end of lead 104 contains temperature sensor 106. It is a commonly available thermoresistive device which is housed within rigid housing 154. Preferably rigid housing 154 is a titanium cylinder which is insulated inside and outside with medical grade silicone rubber. The two terminals of the thermistor within rigid housing 154 are coupled to the two conductors within the body of lead 104. The thermistor is thermally coupled to distal tip 150 of temperature sensor 106 which is preferably comprised of a biocompatible material such as titanium. Distal tip 150 is not insulated to promote heat conduction to the thermistor of temperature sensor 106 and therefore must be of a biocompatible material. Tine structures 152 assist in the chronic attachment of temperature sensor 106 within skeletal muscle 22. Such tine structures are known in the art to be useful in the chronic attachment of pacing leads. Other such attachment devices may also prove useful for skeletal muscle 22.

Figure 5:
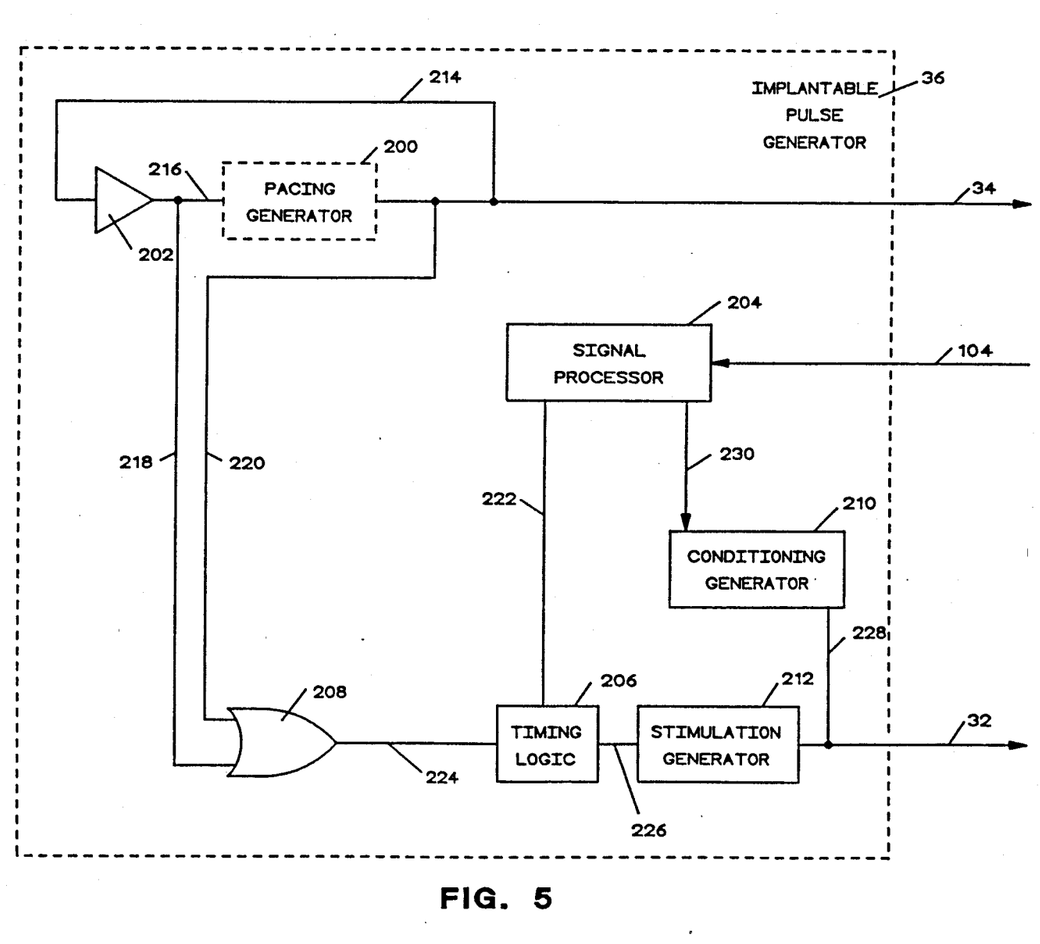
FIG. 5 is a block diagram of the implantable pulse generator.

FIG. 5 is a block diagram of the circuitry of implantable pulse generator 36. Pacing lead 34 electrically couples implantable pulse generator 36 to human heart 100 as is shown in FIG. 1. Pacing generator 200 supplies artificial pacing pulses whenever it determines that a naturally occurring pacing event has not transpired at the correct time. Sensing for such a naturally occurring pacing event is facilitated by sense amplifier 202 which is coupled to pacing lead 34 via line 214. The amplified signal is sent to pacing generator 200 by line 216.

The amplified naturally occurring pacing signal is also sent to or-gate 208 by line 218. Or-gate 208 also receives an indication of an artificial pacing signal via line 220. In either event the output of or-gate 208 on line 224 indicates the time at which a contraction of human heart 100 has been stimulated, whether naturally or artificially.

Timing logic 206 provides a signal via line 226 to notify stimulation generator 212 to produce a pulse to stimulate contraction of skeletal muscle 22. This signal occurs at a predetermined delay after the contraction of human heart 100. The exact amount of this delay is based upon two factors. The first of these is the configuration of the cardiac assist system. As explained above, this delay is necessary to provide the contraction of skeletal muscle 22 at the proper time relative to human heart 100. This delay is very short for the configuration of FIG. 1 and is quite substantial for the configuration of FIG. 3. The second factor is an adjustment provided by signal processor 204 via line 222. This factor is explained in detail below.

Conditioning generator 210 provides the pulses used to condition skeletal muscle 22 as a "slow twitch" muscle as taught by Cox. These pulses are transferred to skeletal muscle 22 by line 228 and lead 32, along with the stimulation pulses of stimulation generator 212. After skeletal muscle 22 has been fully conditioned a taught by Cox, the conditioning pulses may be replaced by maintenance pulses which differ from conditioning pulses by their lower amplitude and hence lower power requirements. The change to maintenance pulses is triggered by signal processor 204 via line 230 under the conditions as discussed below.

Signal processor 204 is coupled to temperature sensor 106 by the two conductors of lead 104 as explained above. Signal processor 204 uses circuitry known in the art to measure the resistance of the thermistor of temperature sensor 106, and therefore, the temperature of skeletal muscle 22. Based upon the temperature sensed, signals are sent via lines 222 and 230 to vary the delay of the stimulation pulses and change to maintenance pulses, respectively.

Figure 6:
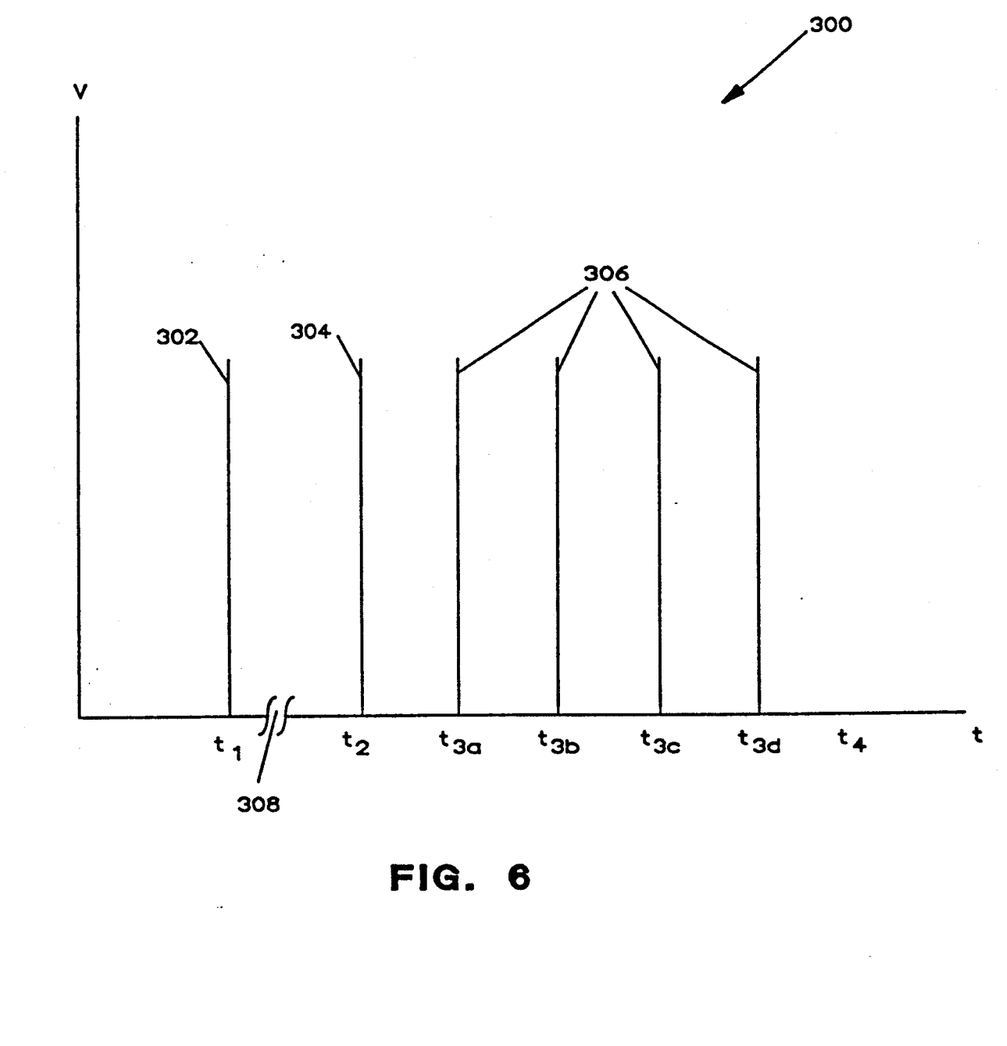
FIG. 6 is a graphical representation of the timing relationship between contractions of the human heart and the pulses produced by the implantable pulse generator.

FIG. is a graphical representation 300 of a single cycle containing a pacing pulse 302 occurring at time t1 and the corresponding pulses transferred to skeletal muscle 22 Stimulation pulse 304 is that pulse which is intended to cause the primary contraction of skeletal muscle 22. It occurs at time t2 following a delay 308. As explained above, delay 308 is in part determined by the configuration of the cardiac assist system and in part by signal processor 204. Following stimulation pulse 304, conditioning/maintenance pulses 306 are generated at times t3a, t3b, t3c, and t3d. These pulses are produced by conditioning generator 210 in accordance with the teaching of Cox.

Figure 7:
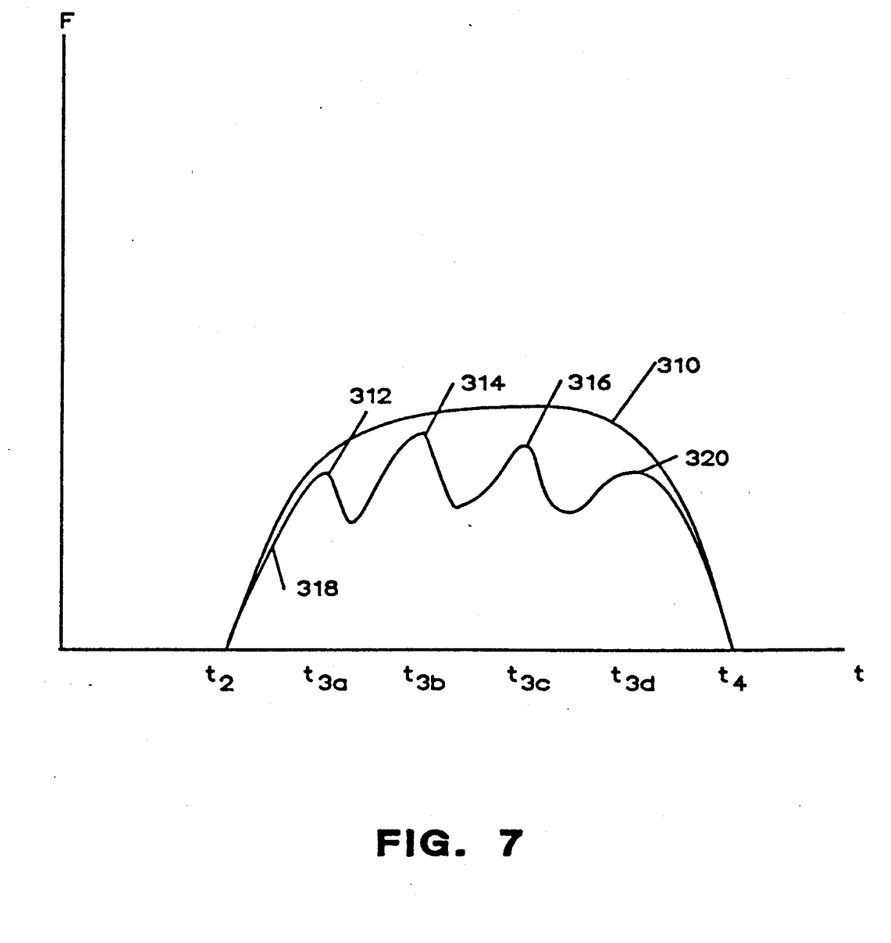
FIG. 7 is a graphical representation of the force produced by conditioned and unconditioned skeletal muscle.

FIG. 7 is a graphical representation of the force of contraction of skeletal muscle 22 for one unconditioned cycle 318 and one conditioned cycle 310. The force curve for the conditioned cycle 310 is smooth and continuous and is representative of a slow twitch muscle. The force curve for the unconditioned cycle 318 is discontinuous and is characteristic of a fast twitch muscle. Force peaks 312, 314, 316, and 320 are secondary contractions corresponding to the conditioning pulses, occurring at times t3a, t3b, t3c, and t3d, respectively. These specific curves show ideal responses. Actual measurement of these specific curves using a thermistor would probably be very difficult.

Figure 8:
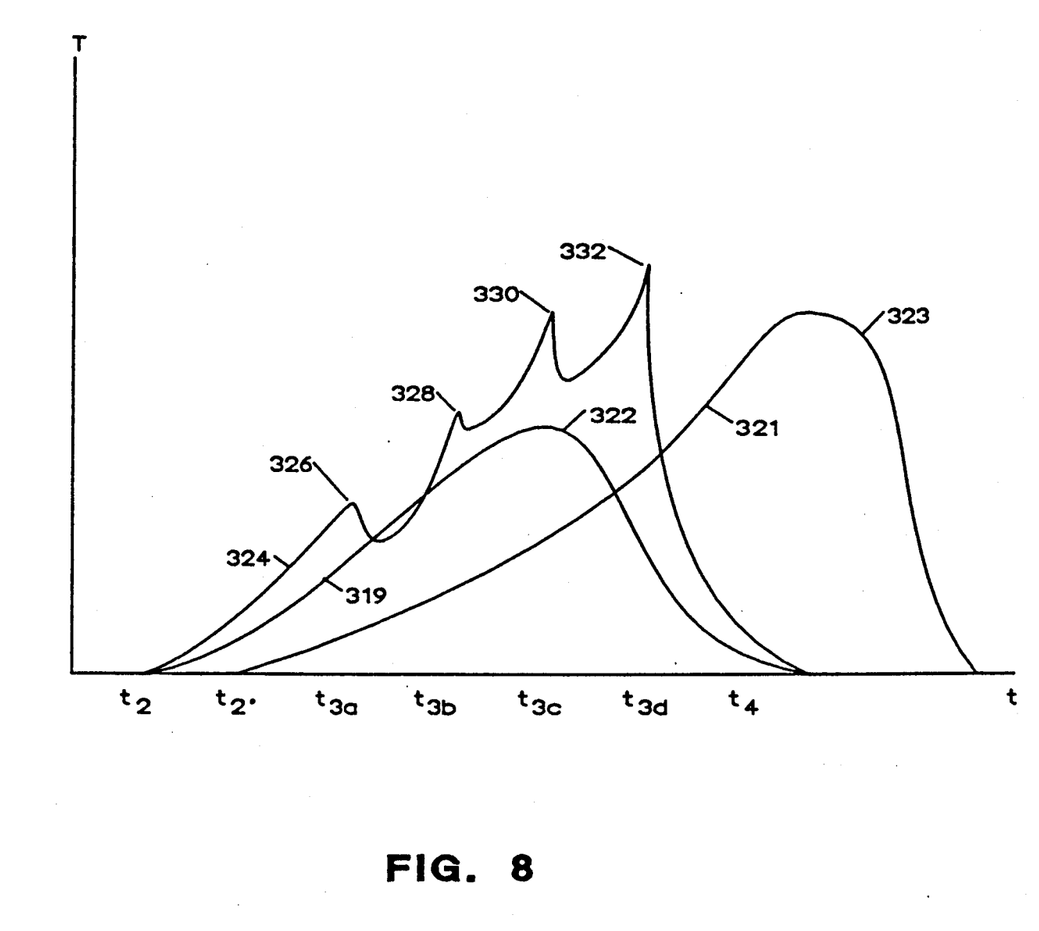
FIG. 8 is a graphical representation of the temperature sensed for unconditioned, conditioned but improperly timed, and conditioned and properly timed skeletal muscle contractions.

FIG. 8 is a graphical representation of the temperature curves measured by temperature sensor 106 under three different situations. Temperature curve 319 corresponds to the ideal situation of a properly timed contraction of a fully conditioned skeletal muscle 22. The two key characteristics of this curve are its smooth and continuous nature and the relatively low peak temperature at peak 322.

Temperature curve 321, on the other hand, although smooth and continuous, is delayed somewhat and reaches a much higher temperature peak 323. This higher temperature peak is readily sensed by signal processor 204 as an improperly timed stimulation pulse. The higher temperature results from the much larger component of isometric and much smaller component of isotonic activity associated with the improperly timed contraction. Upon sensing this elevated temperature peak 323, signal processor 204 notifies timing logic 206 via line 222 to shorten delay 308 (see also FIGS. 5 and 6).

Temperature curve 324 is characteristic of an unconditioned skeletal muscle 22. This temperature curve 324 has a number of relative temperature peaks at 326, 328, 330, and 332. These relative temperature peaks correspond to fast twitch response to the conditioning pulses. Because the skeletal muscle 22 of temperature curve 324 is unconditioned, signal processor 204 must so notify conditioning generator 210 via line 230.

Figure 9:
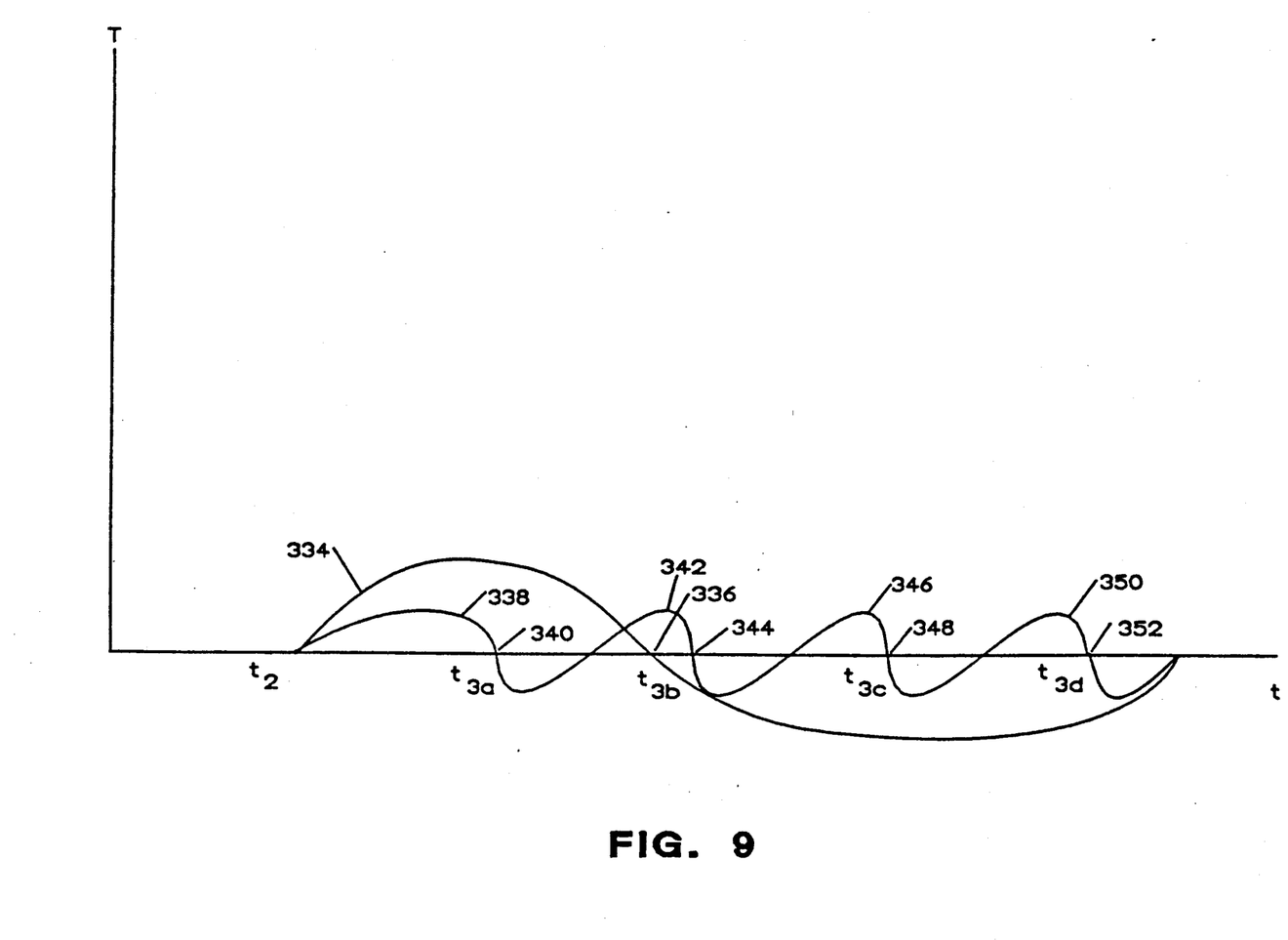
FIG. 9 is a graphical representation of the change in temperature over time for conditioned and unconditioned skeletal muscle.

FIG. 9 is a graphical representation of the differentiated temperature curves 319 ant 324 wherein curve 334 corresponds to curve 319 and curve 338 corresponds to curve 324. Through the use of the differentiated temperature curves, signal processor 204 can much more readily distinguish between conditioned and unconditioned skeletal muscle 22. Because curve 334 represents fully conditioned skeletal muscle 22, it has a smooth and continuous temperature curve as explained above, and the corresponding differentiated curve has a single zero crossing at point 336. Differential curve 338, on the other hand, has zero crossings at 340, 344, 348, and 352.

This is easily detected by signal processor 204 either digitally or by frequency discrimination using well known techniques.

Having thus described the preferred embodiments of the present invention, those of skill in the art will be able to readily apply these teachings to other embodiments without deviating from the scope of the claims hereto attached.

I claim:
1. Apparatus comprising:
   a. a surgically prepared skeletal muscle adapted to be mechanically coupled to a natural human heart having ventricles which contract at a ventricular rate such that contraction of said surgically prepared skeletal muscle assists said natural human heart;
   b. means adapted to be responsively coupled to said natural human heart and said surgically prepared skeletal muscle for stimulating said skeletal muscle in synchrony with contraction of said ventricles to assist said natural human heart; and
   c. means responsively coupled to said stimulating means for measuring a parameter indicative of the efficiency of contraction of said skeletal muscle.

2. Apparatus according to claim 1 further comprising means responsively coupled to said measuring means and said stimulating means for adjusting the timing of said stimulating means to improve the efficiency of said surgically prepared skeletal muscle.

3. Apparatus according to claim 2 wherein said measuring means comprises a temperature sensor.

4. Method of assisting cardiac activity of the ventricles of a natural human heart comprising:
   a. surgically preparing a skeletal muscle;
   b. positioning said skeletal muscle such that synchronous contraction of said skeletal muscle with respect to contraction of said ventricles of said natural human heart assists cardiac activity;
   c. stimulating said skeletal muscle to contract in synchrony with said contraction of said ventricles of said natural human heart using an electrical signal having a plurality of parameters; and
   d. measuring a parameter indicative of the efficiency of said contraction of said skeletal muscle.

5. Method according to claim 4 further comprising automatically modifying at least one of said plurality of parameters of said stimulating step in response to the result of said measuring step and repeating both said stimulating step and said measuring step.

6. Method according to claim 5 wherein said measuring step comprises measuring the temperature of said skeletal muscle.

* * * * *